United States Patent [19]

Friedman

[11] Patent Number: 4,893,508

[45] Date of Patent: Jan. 16, 1990

[54] HUMIDITY SENSING APPARATUS AND METHOD THEREFOR

[75] Inventor: Maurice Friedman, Roslyn, Pa.

[73] Assignee: VIZ Manufacturing Company, Philadelphia, Pa.

[21] Appl. No.: 283,798

[22] Filed: Dec. 13, 1988

[51] Int. Cl.$^4$ .................. G01W 1/02; G01W 1/08
[52] U.S. Cl. ........................ 73/336.5; 333/35
[58] Field of Search ................ 73/29, 336, 336.5; 340/602; 324/61 R; 338/35

[56] References Cited

U.S. PATENT DOCUMENTS

| | | | |
|---|---|---|---|
| 3,926,052 | 12/1975 | Bechtel | 73/336.5 |
| 4,227,411 | 10/1980 | Abramovich | 73/336.5 |
| 4,481,514 | 11/1984 | Beukers et al. | 73/170 R |

FOREIGN PATENT DOCUMENTS 96244  6/1982  Japan .................. 73/336.5

OTHER PUBLICATIONS

James F. Morrissey et al, "Temperature-Induced Errors in the ML-476 Humidity Data", Journal of Applied Meteorology, vol. 9, No. 5, Oct. 1970, pp. 805-808.

Primary Examiner—Hezron E. Williams
Attorney, Agent, or Firm—Howson and Howson

[57] ABSTRACT

A sensing system and method suitable for use in humidity sensing instruments such as radiosondes to determine the true relative humidity of the atmosphere contemporaneously with other parameters at the same altitude as the radiosonde rises or descends. The indicated relative humidity of the air contiguous with a humidity sensing element and the temperature of the humidity sensor and the surrounding air temperature, remote from the sensor, are measured. The true relative humidity of the surrounding air is determined by the product of the indicated relative humidity and the ratio of the saturated vapor pressure at the sensor temperature to that at the surrounding air temperature.

16 Claims, 1 Drawing Sheet

HUMIDITY SENSING APPARATUS AND METHOD THEREFOR

BACKGROUND OF THE INVENTION

The present invention relates in general to humidity sensors, and more particularly to humidity sensors and methods for use thereof in metereological observations, such as by radiosondes or dropsondes.

Radiosondes are either lifted by a balloon from a ground station or dropped with a drogue from a high altitude platform and sense meteorological parameters pertaining to the atmosphere, especially pressure, temperature, humidity, wind speed and direction. These measurements are correlated with the altitude as the radiosonde descends or rises. Since balloon radiosondes typically rise at approximately 300 meters/minute, and drogue radiosondes, referred to as dropsondes, descend at twice that rate, it is essential that they respond rapidly to changes with altitude. However, relative humidity is one of the parameters for which sensors have been more susceptible to measuring lags.

Of the various instruments used for sensing relative humidity, chemical films are particularly suitable for radiosondes. The film, whose electrical resistance changes with exposure to moisture, is deposited on a structural substrate which provides external electrical connections to the film. Being low in mass, the film deposit responds rather rapidly to a change in the moisture content of the surrounding atmosphere; but the substrate, being massive relative to the film deposit, does not reach thermal equilibrium with the surrounding atmosphere as quickly. In fact, the temperature of the film deposit is more nearly the same as that of the substrate since they are so intimately connected. Consequently, the relative humidity indicated by the film deposit is that of the air at the substrate temperature rather than of the surrounding atmosphere. The physics of this phenomenon is such that the warmer the air, the more moisture can exist as a vapor in grains per unit volume before it condenses. Therefore, if the substrate is colder than the surrounding air, the indicated relative humidity will register higher than the actual or "true" humidity of the surrounding air.

This phenomenon can be extended to radiosondes. In standard atmosphere, the air is increasingly colder with altitude through the troposphere up to the lower boundary of the tropopause where the temperature is constant up to the stratosphere where there is an inversion. The air then begins to warm up with further elevation. In the case of a rising radiosonde, the thermal lag of the humidity sensor or "substrate error" is therefore in both directions, i.e. the substrate temperature is higher than the surrounding air temperature through the troposphere, and lower through the stratosphere.

On the other hand, dropsondes are usually dropped from an altitude below the tropopause where there is essentially only a continuous warming of the atmosphere. The thermal lag in the humidity sensor causes the substrate temperature to be always colder than the atmosphere. Hence, the indicated relative humidity will be higher than 100% if the surrounding air is saturated but the substrate temperature is lower. If the surrounding air is very nearly saturated, but the substrate temperature is lower, the relative humidity sensor might, and very often does, indicate 100% when, in fact, it is lower.

In a rapidly falling dropsonde where the substrate temperature stays colder than the air temperature, and the air is saturated or nearly saturated, the problem of accuracy is compounded. At high altitude launches, the temperature at the relative humidity sensor is usually very low, and as it descends the substrate temperature may be lower than the dew point of the air temperature at the lower altitude. Moisture in the air contacting the substrate and the film deposit then condenses on the sensor even though the dew point of the surrounding air is higher than the substrate temperature. Consequently, sensitivity to humidity is impaired due to water and/or ice accumulating on the sensor. If the temperature of the humidity sensor were always above the dew point of the ambient air, no water or ice could accumulate.

Humidity sensors of the prior art have no provision for maintaining the substrate temperature above the dew point while continuously measuring relative humidity. One such sensor, instead, allows for this condition by utilizing a mirror surface on a chilled substrate on which moisture condenses. When a photocell senses the condensation, a thermometer in the substrate measures the dew point from which the relative humidity can be determined according to well-known methods. Such a system is too expensive for routine use in radiosondes, and is incapable of frequent measurements because of the relatively long time interval required to clear the substrate by heating for the next reading.

SUMMARY OF THE INVENTION

Accordingly, it is an object of the present invention to provide a humidity sensor which is particularly suitable for use in meteorological observations and which is highly accurate in rapidly changing temperature environments.

Another object is to provide a method for correcting the indicated relative humidity to reflect the true relative humidity of the surrounding air as a radiosonde ascends or descends through the atmosphere.

Still another object is to provide a system for use in a radiosonde which will reflect the true relative humidity in the atmosphere contemporaneously with other parameters of the atmosphere.

A further object of the invention is to provide a humidity sensor which is compensated for temperature variations in its supporting structure, and which will operate at all surrounding gas mixture temperatures.

A still further object is to provide a highly reliable humidity sensor which is compact, constructed of lightweight state-of-the-art materials, and inexpensive to manufacture and maintain.

Briefly, these and other objects of the invention are accomplished with a relative humidity sensor having a substrate formed into a thin rectangular wafer. Two thick-film resistive elements are deposited on the substrate, one chemically responsive to the relative humidity of a gas mixture contiguous therewith, and the other responsive to the substrate temperature. A thermal element remote from the substrate measures the temperature of the surrounding gas mixture. The ratio of the saturation vapor pressures of the gas mixture at the measured substrate and surrounding mixture temperatures is factored with the measured relative humidity for determining the true relative humidity of the surrounding mixture at any given time. An additional thick-film heating element may also be deposited on the substrate and energized when the relative humidity at the substrate exceeds a predetermined amount. This precludes the possibility of reaching 100% relative humidity where the vapor may condense and possibly freeze on the humidity element, rendering it uselessly inaccurate.

With this arrangement of temperature and humidity elements associated with a single substrate, particularly as applied to radiosondes, it is possible to obtain a very rapid and accurate response to changes in humidity contemporaneously with other measurements, such as during the ascent or descent of a radiosonde.

BRIEF DESCRIPTION OF THE DRAWING

For a better understanding of these and other objects and aspects of the invention, reference may be made to the following detailed description taken in conjunction with the accompanying drawing which is a schematic representation of a preferred embodiment of a relative humidity sensing system according to the invention.

DESCRIPTION OF THE PREFERRED EMBODIMENT

Figure 1:
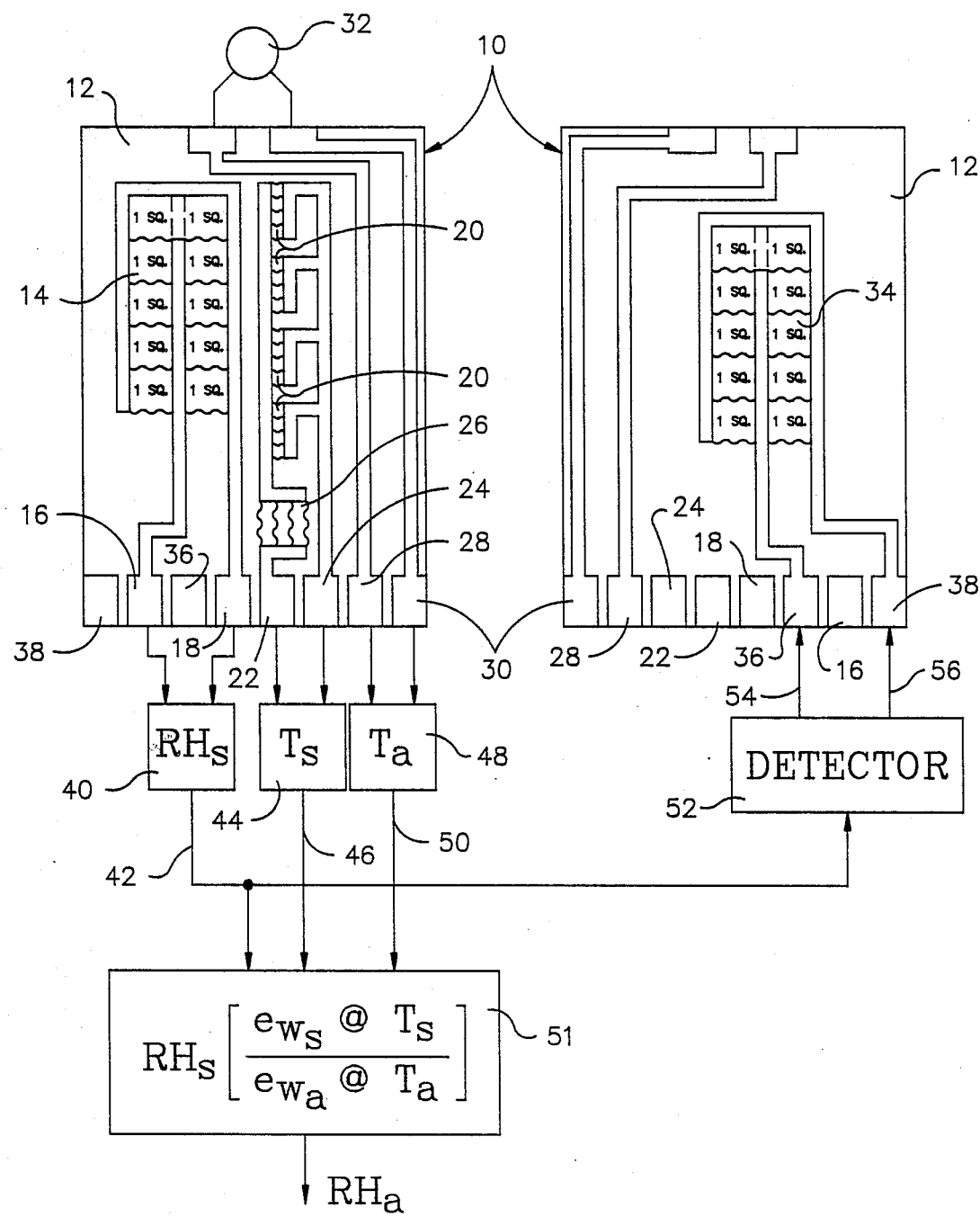

Humidity is defined as the amount of water in the vapor phase present in a gaseous mixture. It may be expressed in many ways, but more often as relative humidity. Physically speaking, it is the amount of moisture by weight in a unit volume of a gas mixture to the amount which the mixture could hold if completely saturated at the mixture temperature. When the relative humidity is unity, the mixture is saturated. In percent relative humidity, %RH, it may also be mathematically expressed as follows:

$$\%RH = \frac{e}{e_w} \times 100 \qquad (1)$$

where $e$ = the vapor pressure at the mixture temperature T, and $e_w$ = saturation pressure at the mixture temperature T.

With this fundamental relationship, the indicated relative humidity $RH_s$ of a mixture contiguous with a humidity sensitive film on a substrate and the true relative humidity $RH_a$ of the surrounding mixture can be expressed as follows:

$$RH_s = \frac{e_s}{e_{Ws}}, \text{ and} \qquad (2)$$

$$RH_a = \frac{e_a}{e_{Wa}}, \qquad (3)$$

where $e_s$ = the vapor pressure at the substrate temperature $T_s$, $e_{ws}$ = the saturation vapor pressure at the substrate temperature $T_s$, $e_a$ = the vapor pressure of the surrounding mixture at temperature $T_a$, and $e_{wa}$ = saturation vapor pressure of the surrounding mixture at temperature $T_a$.

If both mixtures are at the same altitude, their vapor pressure will be equal, i.e. $e_s = e_a$, and equations (2) and (3) may be combined to solve for $RH_a$. Thus, $$RH_a = RH_s \left[ \frac{e_{Ws} \text{ at } T_s}{e_{Wa} \text{ at } T_a} \right]. \qquad (4)$$

The values of the saturation vapor pressures $e_{ws}$ and $e_{wa}$ corresponding to these temperatures are obtained from Table 94, Saturation Vapor Pressure over Water with Temperature, Smithsonian Meteorological Tables, 6th Revised Edition by Robert J. List, Smithsonian Institute, Washington, DC 1958. Accordingly, it is possible to determine the relative humidity of surrounding air by measuring the relative humidity $RH_s$ at the substrate, and the temperatures $T_s$ and $T_a$ of the air at the substrate and in the surrounding atmosphere, respectively.

Referring now to the drawing, there is shown a greatly enlarged representation of the two sides of a humidity sensor 10 electrically connected within a signal processing system, shown in block diagram, according to the invention. As applied to meteorological use, signals from the sensor 10 may be processed partly or entirely within the radiosonde system according to the user's requirements. Sensor 10 comprises a substrate 12 with a chemical thick-film 14 deposited on one side between a pair of electrical conductors 16 and 18. Conventional materials and methods of constructing the sensor 10 are contemplated. In the illustrated embodiment, for example, substrate 12 is a 96% alumina ceramic about ¾" wide by 1" long with screened-on conductors. Conductor 18 extends along the length of the substrate from one end and folds back to form a J-shape path. Conductor 16 extends from the same end and bisects the area between the folded portions of conductor 18. Film 14 may be characterized as a plurality of "squares" of a known resistance per square by which it is possible to select the number required to provide a selected combined resistance or "absolute lock-in value" between the conductors. Deposited on the same side with resistor 14 is a substrate temperature sensor of thick-film resistors 20 connected in parallel between a pair of conductors 22 and 24. Conductor 22 includes a thick-film resistor 26 in series with parallel resistors 20 for trimming the combined resistances across the conductors 22 and 24 to the lock-in value. Substrate 12 also includes conductors 28 and 30 to which a thermistor 32 is connected at their one ends for measuring the air temperature remote from the substrate, hereinafter referred to as the surrounding air temperature. For uniformity in signal processing, it is preferred that the humidity-resistance and temperature-resistance curves, which are defined by well-known polynomial equations, be substantially the same order of magnitude over their operating ranges. This is done by establishing absolute lock-in values, such as 10,000 ohms, for each curve at points along the curves established by industry convention.

The reverse side of substrate 12 includes a heating element having a thick-film resistance heater 34 deposited between conductors 36 and 38. When electrical current is applied, the generated heat transfers into substrate 12 to raise its temperature.

Variations in resistance between conductors 16 and 18 due to changes in relative humidity at substrate 12 are converted by a function generator 40 into a signal on conductor 42 indicative of the relative humidity $RH_s$ of the air contiguous with the sensor 10; variations in resistance between conductors 22 and 24 are converted in a function generator 44 to a signal on conductor 46 indicative of the substrate temperature $T_s$; and variations in resistance between conductors 28 and 30 are converted by a function generator 48 to produce an output signal on conductor 50 indicative of the surrounding air temperature $T_a$. These signals are inputted to a computer 52 in which are stored the equations relating to the saturated vapor pressure tables from which the relative humidity of the air can be determined according to equation (4), supra.

During some meteorological observations, the atmosphere may cool the humidity sensor to a temperature below the dew point of the atmosphere subsequently measured as the radiosonde rises or descends. Moisture in the air will then condense and possibly freeze on the sensor making it completely insensitive to humidity. The present invention provides a means for preventing the indicated relative humidity at the substrate from rising above a predetermined level and causing condensation. This is accomplished by a detector 52 which energizes heater 34 through conductors 54 and 56 when the indicated relative humidity $RH_s$ exceeds a preselected level. A current through resistance heater 34 causes substrate 12 to heat up until the humidity decreases to a preselected level. In some particular cases, the substrate temperature $T_s$ may rise to within 3° to 4° C. of the surrounding air temperature $T_a$. The upper and lower relative humidity levels are selected within a range that will assure a timely response for compensating the thermal lag of the substrate.

Operation of the humidity sensing system will be summarized as applied to a dropsonde launched from a cold tropospheric altitude. In the illustrated embodiment, the set point of detector 52 is chosen to energize heater 34 above 70% indicated relative humidity and turn off at 60%. As the dropsonde descends to a lower elevation, the outputs of function generators 40, 44 and 46 indicate a substrate temperature $T_s$ of −26° C., a surrounding air temperature $T_a$ of −30° C. and an indicated relative humidity $RH_s$ of 65%. Since the indicated relative humidity is below 70%, heater resistor 34 is not energized because there is no risk of condensation on the substrate 12. With the measured signals inputted to computer 51, the true or corrected relative humidity $RH_a$ of the surrounding air is computed according to equation (4) and the measure parameters as follows:

$$RH_a = 65\% \left[ \frac{12.15}{8.37} \right] = 94.34\%$$

where 12.15 and 8.37 are the saturation vapor pressures over water at −26° C. and −30° C., respectively.

If the indicated relative humidity $RH_s$ were above 70%, detector 52 would energize heater 34 to raise the substrate temperature until the indicated relative humidity were lowered to within the range 60%-70%. For example, if the indicated relative humidity were lowered to 60%, the substrate temperature would have increased to −25.1° C. and result in substantially the same corrected $RH_a$, i.e. 94.52%. Thus it can be seen that heating the substrate 12 does not significantly affect the result. That is $$RH_a = 60\% \left[ \frac{12.75}{8.09} \right] = 94.52\%$$

where 12.75 and 8.09 are the saturation vapor pressures over water at −25.1° C. and −30° C., respectively.

Some of the many advantages and novel features of the invention should now be readily apparent. For example, a humidity sensing system and method therefor is disclosed which is particularly useful for meteorological observations. It provides highly accurate relative humidity measurements contemporaneously with other parameters collected at selected altitudes. The relative humidity measurement is not affected by temperatures of adjacent support structure and is adaptable for preventing condensation and possible formation of ice on the humidity sensing element. The same humidity sensing system is useable in a ground sensing instrument, utilizing the heating feature of the invention, to maintain it at a point which is less subject to hysteresis, and thus achieve greater accuracy. The indicated relative humidity is corrected for temperature variations in the supporting structure to record the true humidity of the surrounding atmosphere. The novel sensing system permits the use of well-known state-of-the-art components, materials and manufacturing techniques which are inexpensive and have established reliability.

Obviously many modifications and variations of the present invention are possible in light of the above teachings. It is therefore to be understood that within the scope of the appended claims, the invention may be practiced otherwise than as specifically described.

I claim:

1. A humidity sensing system, comprising, in combination:

a support;

first means deposited on said support for continuously producing a first signal indicative of the relative humidity above the dew point temperature of a gas mixture contiguous thereto;

second means deposited on said support for producing a second signal indicative of the temperature of said support;

third means for producing a third signal indicative of the temperature of the gas mixture at a point spaced from said support; and computer means responsive to said signals for determining the relative humidity of the mixture at the spaced point as a function of the first signal and the ratio of saturation vapor pressures of the mixture at the respective temperatures indicated by the second and third signals.

2. A humidity sensing system according to claim 1 further comprising:

fourth means responsive to said first signal for heating said support when the relative humidity of the mixture contiguous with the support exceeds a selected level.

3. A humidity sensing system according to claim 1 wherein:

said computer means determines the relative humidity $RH_m$ of the mixture at the point according to the equation $$RH_m = RH_s \left[ \frac{e_{Ws}}{e_{Wa}} \right]$$

where
$RH_s$ = relative humidity of the mixture contiguous with the support means,
$e_{ws}$ = saturation vapor pressure at the temperature of said support, and
$e_{wa}$ = saturation vapor pressure of the mixture at the spaced point.

4. A humidity sensing system according to claim 1 wherein:
said support includes a substrate composition of alumina formed into a thin rectangular wafer;
said first means includes a thin film deposited on one side of said support electrically responsive to humidity, a first electrode extending from ne end of said substrate and folding back to form a J-shape path, a second electrode extending from said one end of said substrate for bisecting the area between the folded portions of said first conductor, and a first resistor ink deposited between said first and second electrodes for varying the resistance as a function of humidity; and
said second means includes a thin film resistance means deposited on said one side of said support electrically responsive to temperature.

5. A humidity sensing system according to claim 4 wherein said second means further includes:
a third electrode extending from said one end of said substrate and including a gap near said one end;
a fourth electrode extending from said one end of said substrate and folding back at spaced intervals along the length thereof to form a plurality of connectors juxtaposed from said third electrode;
a second resistor ink deposited between each of said connectors and said third electrode suitable for varying the resistance as a function of temperature; and
a third resistor ink deposited in said gap for trimming the effective resistance of said second resistor ink.

6. A humidity sensing system according to claim 2 wherein said fourth means includes:
a detector for producing an electrical current output when the humidity exceeds the selected level;
a first electrode extending from said one end of said substrate and folding back to form a J-shape path;
a second electrode extending from said one end of said substrate for bisecting the area between the folded portions of said first electrode;
a resistor ink deposited between said first and second electrodes for heating said substrate when a current is applied thereto; and
said first and second electrodes being connected to the current output of said detector.

7. In radiosonde suitable for use in measuring atmospheric conditions in the air with changes in altitude, an improved humidity sensing system, comprising, in combination:
a substrate formed to be carried by the radiosonde;
a first sensor deposited on said substrate for continuously producing an output indicative of the relative humidity above the dew point temperature of the air contiguous thereto;
a second sensor deposited on said substrate for producing an output indicative of the temperature of said substrate;
a third sensor for producing an output indicative of the temperature of the air at a point spaced from said substrate; and
a computer operatively connected to said sensors for determining the relative humidity of the mixture at the spaced point as a function of the first signal and the ratio of saturation vapor pressures of the mixture at the respective temperatures indicated by the second and third signals.

8. A humidity sensing system according to claim 7 further comprising:
heater means responsive to said first sensor output for heating said substrate when the relative humidity of the mixture contiguous with said substrate exceeds a selected level.

9. A humidity sensing system according to claim 7 wherein:
said computer determines the relative humidity $RH_a$ of the mixture at the point according to the equation $$RH_a = RH_s \left[ \frac{e_{Ws}}{e_{Wa}} \right]$$

where
$RH_s$ = indicated relative humidity of the mixture contiguous with said substrate,
$e_{ws}$ = saturation vapor pressure at the temperature of said support, and
$e_{wa}$ = saturation vapor pressure of the mixture at the spaced point.

10. A humidity sensing system according to claim 7 wherein:
said substrate is a composition of alumina formed into a thin rectangular wafer;
said first sensor includes a thin-film resistor deposited on one side of said substrate responsive to humidity, a first electrode extending from one end of said substrate and folding back to form a J-shape path, and a second electrode extending from said one end of said substrate for bisecting the area between the folded portions of said first conductor; and
said second sensor includes a thin-film resistor deposited on said one side of said substrate responsive to temperature.

11. A humidity sensing system according to claim 10 wherein said first sensor further includes:
a first ink deposited between said first and second electrodes for varying the resistance as a function of humidity.

12. A humidity sensing system according to claim 10 wherein said second sensor further includes:
a third electrode extending from said one end of said substrate with a gap near said one end; and
a fourth electrode extending from said one end of said substrate and folding back at spaced intervals along the length thereof to form a plurality of connectors juxtaposed from said third electrode.

13. A humidity sensing system according to claim 12 wherein said second sensor further includes:
a second ink deposited between each of said connectors and said third electrode suitable for varying the resistance as a function of temperature; and a third ink deposited in said gap for trimming the effective resistance of said second ink.

14. A humidity sensing system according to claim 8 wherein said heater means includes:
   a detector for producing an electrical current output when the humidity exceeds the selected level;
   a first electrode extending from said one end of said substrate and folding back to form a J-shape path;
   a second electrode extending from said one end of said substrate for bisecting the area between the folded portions of said first electrode;
   a resistor ink deposited between said first and second electrodes for heating said substrate when a current is applied thereto; and
   said first and second electrodes being connected to the current output of said detector.

15. A method for accurately determining the relative humidity of the atmosphere contemporaneously with altitude of an ascending or descending sonde, comprising the steps of:
   measuring continously at a selected altitude the relative humidity above the dew point temperature of the air contiguous with a humidity sensitive element mounted on a support within the sonde;
   measuring at the selected altitude the temperature of the support at the selected altitude;
   measuring the temperature of the air remote from the support at the selected altitude; and
   determining the relative humidity of the air remote from the support at the selected altitude as a function of the measured relative humidity and the ratio of a saturated vapor pressure of the air at the temperature of the support to a saturated vapor pressure of the air remote from said support.

16. A method for accurately determining the relative humidity of a gas mixture with a sensor at a temperature different from the mixture, comprising the steps of:
   measuring the relative humidity $RH_s$ of the mixture contiguous with the sensor;
   measuring the temperatures of the sensor and the mixture; and
   computing the relative humidity $RH_a$ of the mixture according to the equation $$RH_a = RH_s \left[ \frac{e_{ws}}{e_{wa}} \right]$$

where
$e_{ws}$ = saturated vapor mixture at the temperature of the sensor, and
$e_{wa}$ = saturated vapor pressure of the mixture.

* * * * *